(12) United States Patent
Zhu et al.

(10) Patent No.: US 9,360,474 B2
(45) Date of Patent: Jun. 7, 2016

(54) MULTI-LAYER DEVICE FOR SELECTIVELY DETERMINING MAGNESIUM ION

(71) Applicant: OPTI Medical Systems, Inc., Westbrook, ME (US)

(72) Inventors: Peter Chaoquan Zhu, Los Altos, CA (US); Yingzi Wu, Johns Creek, GA (US)

(73) Assignee: OPTI Medical Systems, Inc., Westbrook, ME (US)

( * ) Notice: Subject to any disclaimer, the term of this patent is extended or adjusted under 35 U.S.C. 154(b) by 504 days.

(21) Appl. No.: 13/689,350

(22) Filed: Nov. 29, 2012

(65) Prior Publication Data

US 2014/0147876 A1    May 29, 2014

(51) Int. Cl.
*G01N 33/52* (2006.01)
*C07D 221/14* (2006.01)
*G01N 31/22* (2006.01)
*G01N 33/84* (2006.01)

(52) U.S. Cl.
CPC ............ *G01N 33/526* (2013.01); *C07D 221/14* (2013.01); *G01N 31/22* (2013.01); *G01N 33/52* (2013.01); *G01N 33/84* (2013.01)

(58) Field of Classification Search
CPC ... G01N 33/84; G01N 31/22; G01N 21/6428; G01N 21/645; G01N 33/525; G01N 31/226; A61L 2/28
USPC .......................................... 436/79; 422/82.08
See application file for complete search history.

(56) References Cited

U.S. PATENT DOCUMENTS

| | | | |
|---|---|---|---|
| 4,367,072 A | 1/1983 | Vogtle et al. | |
| 4,603,209 A | 7/1986 | Tsien et al. | |
| 4,774,339 A | 9/1988 | Haugland et al. | |
| 5,215,925 A * | 6/1993 | Babb ..................... | C07C 317/00 436/74 |
| 5,310,888 A * | 5/1994 | Bloczynski et al. .......... | 534/767 |
| 5,397,710 A * | 3/1995 | Steinman ............. | G01N 33/521 422/423 |
| 5,516,911 A | 5/1996 | London et al. | |
| 5,952,491 A | 9/1999 | Leiner et al. | |
| 5,968,833 A * | 10/1999 | Furuta et al. ..................... | 436/79 |
| 6,046,055 A | 4/2000 | Wolfbeis et al. | |
| 6,171,866 B1 | 1/2001 | He et al. | |
| 6,211,359 B1 * | 4/2001 | He et al. ........................ | 540/469 |

(Continued)

FOREIGN PATENT DOCUMENTS

| | | |
|---|---|---|
| EP | 0 207 392 A2 | 1/1987 |
| WO | WO-00/66265 | 11/2000 |
| WO | WO 2006/058778 A2 | 6/2006 |

OTHER PUBLICATIONS

Berry, et al., "Enzymatic Determination of Sodium in Serum", Clin. Chem., 1988, vol. 34, No. 11, pp. 2295-2298.

(Continued)

*Primary Examiner* — Krishnan S Menon
*Assistant Examiner* — Dwan A Gerido
(74) *Attorney, Agent, or Firm* — Gilberto M. Villacorta; Yogeeta Jadhav; Foley & Lardner LLP (57) ABSTRACT

The invention relates to devices comprising a sensor layer capable of binding magnesium ions and a scavenging layer that preferentially binds to calcium ions in the presence of both magnesium ions and calcium ions. The sensor layers can comprise known or novel luminionophores. The invention further relates to methods of selectively detecting magnesium ion concentration in the presence of calcium ions.

21 Claims, 4 Drawing Sheets

(56) References Cited

U.S. PATENT DOCUMENTS 6,706,528 B2 * 3/2004 London .................. G01N 31/22
436/172
2002/0059684 A1 5/2002 Diwu et al.
2007/0259438 A1 11/2007 He et al.

OTHER PUBLICATIONS

He, et al. "A Fluorescent Sensor with High Selectivity and Sensitivity for Potassium in Water", J. Am. Chem. Soc., 2003, vol. 125, pp. 1468-1469.

He, et al., "A Fluorescent Chemosensor for Sodium Based on Photoinduced Electron Transfer", Anal. Chem., 2003, vol. 75, pp. 549-555.

International Search Report in PCT/US2013/071004 dated May 12, 2014.

Lakowicz, "Topics in Fluorescence Spectroscopy", Probe Design and Chemical Sensing, 1994, vol. 4.

International Preliminary Report on Patentability in PCT/US2013/071004 dated Jun. 11, 2015, 13 pages.

Extended European Search Report mailed Mar. 30, 2016 in related European Application No. 13858809.0 (6 pgs.).

* cited by examiner

FIGURE 4

MULTI-LAYER DEVICE FOR SELECTIVELY DETERMINING MAGNESIUM ION

BACKGROUND OF THE INVENTION

The invention first relates to a device comprising a substrate, sensor layer capable of binding magnesium ions and a scavenging layer that preferentially binds to calcium ions in the presence of both magnesium ions and calcium ions. The present invention also relates to a method of determining the concentration of magnesium ions in a sample wherein the luminoionophore is contacted with magnesium ion in a sample, wherein the intensity of at least one fluorescence emission changes and the concentration of magnesium ion is calculated based on the change in the intensity of the emission. The present invention also relates to novel luminoionophores, comprising a luminophoric moiety and an ionophoric moiety, capable of binding magnesium.

The accurate measurement of physiologic cations, such as sodium, potassium, lithium, calcium, and magnesium, is essential in clinical diagnosis. Traditionally, these ions were determined in plasma or serum using ion-selective electrodes (ISE), which are very cumbersome to use and costly to maintain. Serious drawbacks of electrochemical measuring arrangements are the requirement of a reference element, sensitivity towards electrical potentials and electromagnetic interference.

An alternative enzymatic method is based on the activation of β-Galactosidase by cations (Berry et al., *Clin. Chem.*, 34/11, 1988 2295-2298). However, the high cost and poor stability of the enzyme preclude its extensive application in clinical laboratories. Therefore, the development of practical and inexpensive colorimetric reagents for the clinical determination of these ions in biological fluids remains an important area of research.

U.S. Pat. No. 4,367,072 describes a process for the determination of metal ions using simple crown ethers as ion-binding units. However, the binding lacks sufficient specificity to be useful for many practical applications, such as clinical applications, in which the indicator has to discriminate between ions with very similar properties, e.g., sodium versus potassium or magnesium versus calcium.

U.S. Pat. Nos. 6,211,359; 5,952,491; and 6,171,866 (each of which is hereby individually incorporated by reference in its entirety) report ionophores for potassium, sodium, and calcium, respectively. These ionophores have π-electron conjugated nitrogen and are coupled to a fluorophore or luminophore to make fluorophore-ionophore or luminophore-ionophore sensors where the respective ions are detected by measuring fluorescence or luminescence emission. All three ionophores have been shown to be very selective in determination of potassium, sodium, and calcium in whole blood, respectively (see He et. al. *Anal. Chem.* Vol. 75, 2003, 449-555; and *J. Am. Chem. Soc.* vol. 125, 2003, 1468-1469), thus showing that the ionophores are effective at physiological pH. However, these publications do not provide for an ionophore that selectively binds magnesium.

The invention relates to determination of ions by the luminescence method based on the reversible binding of cations to a cation-selective ionophore and the so-called "PET effect" (photoinduced electron transfer) between the ionophoric and a luminophoric moiety. Determination of other ions by similar methods is described in U.S. Pat. Nos. 6,211,359; 6,171, 866; and 5,952,491, which are each hereby incorporated by reference in their entirety. The cation-selective ionophore may in some instances be selective for more than one cation, but one or more cations may be excluded from binding with the ionophoric moiety by providing an additional selective ionophore, which is selective for the ion to be excluded, in a manner so that the ions must contact the selective filtering ionophore prior to contacting the ionophoric and a luminophoric moiety that shows PET effect.

The so-called "PET effect" denotes the transfer, induced by photons, of electrons from the ionophoric moiety to the luminophoric moiety, which leads to a decrease in the (relative) luminescence intensity and the luminescence decay time of the luminophore. Absorption and emission wavelengths, however, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore the PET effect is partially or completely inhibited, which results in an increase in the relative luminescence intensity and an increase in the luminescence decay time of the luminophoric moiety. Hence, one can deduce the concentration or the activity of a desired ion by measuring the luminescence properties, e.g., relative luminescence intensity and/or luminescence decay time. Activities can be related to concentrations via known Debye-Huckel formulae.

From U.S. Pat. No. 5,516,911, fluorescent indicators based on fluorinated BAPTA derivatives are known. These indicators generally have $K_d$ values in the millimolar range. These fluorescent indicators, however, suffer from a relatively complicated synthesis of the fluorinated BAPTA derivatives.

Moreover, the known ionophores based on BAPTA or on derivatives thereof in an aqueous environment and at normal ambient temperatures are previously shown to exhibit some chemical instability (see, e.g., U.S. Pat. No. 4,603,209, column 26, lines 40-46). This is particularly disadvantageous in determination procedures using optical sensors in measuring situations requiring a high shelf life (durability) of the sensor or where, for monitoring purposes, one sensor is to be used for measuring over prolonged time periods. Often these compounds display smaller $K_d$ values for cations other than magnesium, such as calcium.

The present invention avoids and overcomes the disadvantages and problems in the prior art. The present invention has as its object to provide luminoionophores and devices for the optical determination of magnesium ions, whose ionophores are more easily synthesizable, and can be covalently bound to suitable luminophores when in electronically decoupled condition. Furthermore, the ionophores need not show high selectivity for magnesium ions because a blocking layer comprising an ionophore which preferentially binds to an alternate competing cation, such as calcium, can be installed between the luminoionophore and the solution containing cation.

In addition, the luminoionophores may be bound to a hydrophilic polymer material by means of a chemical group in order to use them in optical sensors.

The luminoionophore should not exhibit inherent pH dependence in the expected pH range of the sample and should be excitable by light of commercially available LEDs, for example at wavelengths >420 nm. These luminoionophores should, in addition, be chemically stable in an aqueous environment even at high ambient temperatures and over prolonged time periods.

SUMMARY OF THE INVENTION

The present invention provides a device comprising a substrate, sensor layer capable of binding magnesium ions and a scavenging layer that preferentially binds to calcium ions in the presence of both magnesium ions and calcium ions. The present invention also provides a method of determining the concentration of magnesium ions in a sample wherein the luminoionophore is contacted with magnesium ion in a sample, wherein the intensity of at least one fluorescence emission changes and the concentration of magnesium ion is calculated based on the change in the intensity of the emission. The present invention also relates to novel luminoionophores, comprising a luminophoric moiety and an ionophoric moiety, capable of binding magnesium.

In one embodiment, the device for selectively measuring the presence of magnesium ions of the invention comprises a substrate, a sensor layer comprising a luminoionophore that is capable of binding magnesium ions and that is optionally immobilized on a solid support and a scavenging layer that preferentially binds to calcium ions in the presence of both magnesium ions and calcium ions, wherein the luminoionophore exhibits luminescence at a first intensity and wherein upon contacting said device with a solution containing magnesium ions the luminoionophore exhibits luminescence at a second intensity that is different from the first intensity in an amount that is in proportion to the concentration of magnesium ion present in the solution.

In some embodiments, the luminoionophore is a known compound. In other embodiments the luminoionophore is a novel compound as disclosed herein.

In another embodiment, the novel luminionophores of the invention is a compound that conforms to Formula (I)

(I)

where, A, B, and C are independently selected from the group consisting of hydrogen, —OCH$_2$COOR', and —N(CH$_2$COOR')$_2$, wherein one or more of A, B and C is independently selected from the group consisting of —OCH$_2$COOR' and —N(CH$_2$COOR')2, wherein R' is selected from the group consisting of hydrogen, C$_1$-C$_{12}$-alkyl, and a cation.

X and Y, in each instance where they appear, are independently selected from the group consisting of hydrogen, hydroxyl, halogen, ethoxy, methoxy, amine and —COOR'.

v is an integer selected from 0, 1, 2, 3 and 4.

Z is a luminophoric moiety.

The invention further provides a method of determining the concentration of magnesium ions in a sample comprising: (a) measuring a fluorescence emission of a mixture comprising a luminoionophore that is capable of binding magnesium ions and a compound that displays a preferential binding affinity for calcium ions when in the presence of both calcium ions and magnesium ions to obtain a first intensity; (b) contacting the mixture of step (a) with the sample; whereby the first intensity changes; (c) measuring the intensity of at least one fluorescence emission to obtain a second intensity; (d) deriving the concentration of magnesium ion in the sample based, in part, on the difference between the first and second intensities.

In other embodiments, the novel luminionophore of the invention is a compound that conforms to Formula (II):

wherein each instance of R is independently hydrogen, C$_1$-C$_{12}$alkyl, or a cation.

A is (CXY)$_n$ wherein n is an integer selected from 0, 1, 2, 3, and 4 and wherein each instance of X and Y is independently selected from the group consisting of hydrogen, hydroxyl, halogen, ethoxy, methoxy, amine and —COOR.

Z is NH or O.

Q is a hydrogen, C$_1$-C$_{12}$-alkyl, cation or solid support.

In other embodiments, the novel luminionophore of the invention is a compound that conforms to Formula (III):

wherein each instance of R is independently hydrogen, C$_1$-C$_{12}$-alkyl, or a cation.

A is —(CHOH)— or a bond.

Q is a hydrogen, C$_1$-C$_{12}$-alkyl, cation or solid support.

DETAILED DESCRIPTION OF THE INVENTION

As used herein, the terms have the following meanings:

The term "alkyl" as used herein refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents.

The term "alkoxy" as used herein refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "halogen" as used herein refers to —F, —Cl, —Br and/or —I.

The term "luminoionophore" as used herein refers to a compound comprising at least one ionophore and at least one luminophore As used herein luminoionophore may include fluoroionophores, which comprise at least one ionophore and at least one fluorophore.

Examples of lipophilic groups are substituted and unsubstituted ($C_1$-$C_{20}$) alkyl groups and ($C_1$-$C_{20}$)alkoxy groups.

Examples hydrophilic groups are ($C_1$-$C_{17}$)alkyl groups having carrying at least one hydroxyl group and/or functional groups which, at the pH of the measuring solution, are present in a dissociated condition. Examples of such functional groups are carboxylic acids, sulfonic acids, and phosphoric acids.

Examples of reactive groups for coupling to aminofunctionalized polymers, for example, aminocellulose and aminofunctional polyacrylamides, are known, for example, from U.S. Pat. No. 4,774,339, Table 4, which is hereby incorporated by reference.

A luminophoric moiety or luminophore may be any moiety by which, in combination with the ionophoric moiety, a PET effect can be achieved. A great number of luminophoric moieties are known from the literature, which, in combination with the ionophore, give a PET effect or, in principle, are suitable for that purpose. Additional example of luminophoric moieties is a luminescent metal ligand complex. Luminescent long-lifetime transition metal ligand complexes with α-diimine ligands selected from the group of 2,2'-bipyridine, 1,10-phenanthroline, and 4,7-diphenyl-1,20-phenanthroline, which ligands contain, for instance, a central atom of the group consisting of ruthenium(II), osmium(II), iridium(III) and rhodium(III).

A Mg dye or magnesium dye may refer to a luminoionophore that shows binding affinity for magnesium and is or may become incorporated into a device of the present embodiments.

The following abbreviations are used herein and have the indicated definitions: NMR is nuclear magnetic resonance; THF is tetrahydrofuran; TLC is thin layer chromatography; EA is ethyl acetate; DBU is 1,8-Diazabicyclo[5.4.0]undec-7-ene; Boc is tert-butyloxycarbonyl; NMP is N-methyl-2-pyrrolidone; TFA is trifluoroacetic acid; DMAP is 4-dimethylaminopyridine; DIPEA is N,N-diisopropylethylamine; MTBE is methyl tert-butyl ether; and NMP is N-methyl-2-pyrrolidone.

Device of the Invention

The present invention provides a device comprising a substrate, sensor layer capable of binding magnesium ions and a scavenging layer that preferentially binds to calcium ions in the presence of both magnesium ions and calcium ions.

The substrate comprises a solid material that is suitable for supporting the deposition of other layers of the device thereupon. In some embodiments the substrate is not opaque to at least one fluorescence spectra emitted by the sensor layer. In some embodiments, the substrate can comprise a high-clarity polymer, for example, the polymer sold under the trademark Melinex® 505. In some embodiments, the substrate is pretreated to promote adhesion of at least one additional layer of the device such as for example the sensor layer. Pretreatment may include, for example, applying a D4 hydrogel layer in between the substrate and the sensor layer for better adhesion of these two.

The sensor layer capable of binding magnesium ions comprises at least one compound that provides a change in spectral emission when contacted with magnesium ion. This compound may be a luminionophore wherein the ionophoric moiety binds to magnesium ions. In some embodiments, the sensor layer comprises a known compound that exhibits a high affinity for magnesium ion and exhibits and increase in fluorescence emission intensity when contacted with magnesium ion. In one embodiment, the sensor layer comprises the known compound 2,2'-(4-(3-carboxylato-4-(2,7-dichloro-6-oxido-3-oxo-3H-xanthen-9-yl)benzamido)-2 (carboxylatomethoxy)phenylazanediyl)diacetate, which is sold under the trademark Magnesium Green™, or Mag-Fura-2™, Mag-Indo-1™, and Mag-fluo-4™. In other embodiments, the sensor layer comprises a luminionophore of a formula disclosed herein. For example, the sensor layer comprises at least one compound selected from Formula (I), Formula (II), and/or Formula (III).

The sensor layer may comprise compounds in addition to the luminionophore to aid in deposition on the substrate. In one embodiment the luminionophore of the sensor layer is deposited directly on the substrate. In another embodiment, the luminionophore of the sensor layer is covalently bound to a solid support, such as for example an aminofunctionalized polymer, which can then be deposited on the substrate. By way of non-limiting example, the solid support may be materials known in the art, such as aminocellulose and aminofunctional polyacrylamides. In an exemplary embodiment the solid support comprises 3-amino-2-hydroxypropyl cellulose (AHPC) fiber. In some embodiments, the bound or unbound luminionophore may be dispersed in a known compound, such as D4 or D6 hydrogel, to aid in the uniform deposition on the substrate.

The scavenging layer of the embodied devices preferentially binds to calcium ions in the presence of both magnesium ions and calcium ions. The layer preferentially comprises at least one compound that displays a smaller dissociation constant ($K_d$) with calcium ions than with magnesium ions, and additionally has fast complexation kinetics for calcium ions and structural stability when incorporated into the device. In some embodiments the scavenging layer comprises BAPTA or a known BAPTA, EGTA (ethylene glycol tetraacetic acid), oxalate derivative, such as sodium oxalate, or homologue.

The embodied devices may optionally comprise one or more additional layers. In some embodiments, the device comprises an additional opaque optical isolation layer, such as for example carbon black. In some embodiments the additional optical isolation layer is incorporated into the scavenging layer so that there is only one deposition of a scavenging layer comprising an optical isolation substrate, such as carbon black. In some embodiments, an additional layer, such as an optical isolation layer may be dispersed in a compound to aid in the deposition on the substrate, such as D4 or D6 hydrogel.

After deposition of the layers, the device is stored or cured at room temperature, which is typically suitable to remove water and prevent contamination with water vapor followed by storage at temperatures below room temperature.

In another embodiment, the device is incorporated into a known pharmaceutical device, such as for example an OPTi LION cassette.

Compounds of the Invention

The present invention provides novel compounds of Formula (I) referred to as "luminoionophores"

(I)

wherein A, B, C, X, Y, v and Z are as defined above.

In some embodiments, a luminoionophore of the present invention changes its luminescence properties in an amount that is in proportion to the concentration of magnesium ion present in a mixture comprising magnesium ions and the luminoionophore, where the luminescence property can be relative luminescence intensity, time-dependent luminescence intensity, or phase shift.

In some embodiments, the luminoionophoric moiety Z in Formula (I) is selected from the group consisting of Formula (a), (b), and (c) as described below.

In some embodiments, Z is a group of Formula (a), (a)

wherein $R^3$, $R^4$, $R^5$, $R^6$, $R^7$ $R^8$, and $R^9$ are independently selected from the group consisting of hydrogen, a lipophilic group, a hydrophilic group and a reactive group for coupling to a polymer; wherein at least one of $R^3$, $R^4$, $R^5$, $R^6$, $R^7$, and $R^8$ is a —NH-group through which Z is bound to the group —(CXY)$_v$—.

In other embodiments, Z is a group of Formula (b), (b)

wherein $R^{10}$, $R^{11}$, $R^{12}$, $R^{13}$, $R^{14}$, $R^{15}$, $R^{16}$, and $R^{17}$ are independently selected from the group consisting of —OH, —OR$^{18}$, wherein R$^{18}$ is selected from the group consisting of a hydrophilic group, a lipophilic group, —O—R$^{19}$-G, wherein R$^{19}$ is a hydrophilic or a lipophilic group and G is a reactive group for coupling to a polymer, and —(CH$_2$)$_w$—COOH, wherein w is an integer between 0 and 17; wherein at least one of $R^{10}$, $R^{11}$, $R^{12}$, $R^{13}$, $R^{14}$, $R^{15}$, $R^{16}$, and $R^{17}$ represents a bond through which Z is bound directly to the ionophoric moiety.

In other embodiments, Z can be a group of Formula (c):

(c)

wherein $R^{20}$, $R^{21}$, $R^{22}$, $R^{23}$, $R^{24}$, $R^{25}$ and $R^{26}$ are independently selected from the group consisting of hydrogen, a lipophilic group, a hydrophilic group and a reactive group for coupling to a polymer or a biomolecule, and wherein R$^{21}$ may form an aromatic ring system together with R$^{22}$, and R$^{25}$ optionally forms an aromatic ring system together with R$^{26}$; and wherein at least one of $R^{20}$, $R^{21}$, $R^{22}$, $R^{23}$, $R^{24}$, $R^{25}$ and $R^{26}$ represents a chemical bond through which Z is bound to the group —(CXY)$_v$—.

In Formula (c), R$^{21}$ may form an aromatic ring system together with R$^{22}$ and R$^{25}$ may form an aromatic ring system together with R$^{26}$.

In Formula (c), at least one of $R^{20}$, $R^{21}$, $R^{22}$, $R^{23}$, $R^{24}$, $R^{25}$ and R$^{26}$ represents a chemical bond through which Z is bound to the group —(CXY)$_v$—.

In other embodiments, Z has the general formula (a) and one of $R^5$ and $R^6$ is —NH and the other is selected from the group consisting of hydrogen, a lipophilic group, a hydrophilic group and a reactive group for coupling to a polymer.

In still other embodiments, Z has the general formula (b) and R$^{14}$ is a bond.

In some embodiments, Z has the general formula (c) and R$^{23}$ is a bond, and R$^{22}$ and R$^{24}$ are independently hydrogen or methyl.

In some embodiments, the luminoionophore is a compound of Formula (II)

(II)

wherein each instance of R is independently hydrogen, $C_1$-$C_{12}$-alkyl, and cation, A is $(CXY)_n$ wherein n is an integer selected from 0, 1, 2, 3, and 4 and wherein each instance of X and Y is independently selected from the group consisting of hydrogen, hydroxyl, halogen, ethoxy, methoxy, amine and —COOR.

Z is NH or O.

Q is a hydrogen, $C_1$-$C_{12}$-alkyl, cation or solid support.

In some embodiments, the luminoionophore is a compound of Formula (III)

(III)

wherein each instance of R is independently hydrogen, $C_1$-$C_{12}$-alkyl, or a cation.

A is —(CHOH)— or a bond.

Q is a hydrogen, $C_1$-$C_{12}$-alkyl, cation or a solid support.

Specific examples of compounds of Formula (II) and Formula (III) are provided below:

-continued

It would be recognized by one skilled in the art that the Boc protecting groups may be removed to affix or immobilize the compound to a polymeric support, or that the alkyl and/or hydroxyl groups of the acids of the ionophore may deprotected or deprotonated and chelated to a cation, such as magnesium.

Methods of the Invention

The invention also provides methods of determining magnesium ion in a sample comprising calcium ions and magnesium ions. In one embodiment, the method of determining the concentration of magnesium ions in a sample comprises (a) measuring a fluorescence emission of a mixture comprising a luminoionophore that is capable of binding magnesium ions and a compound that displays a preferential binding affinity for calcium ions when in the presence of both calcium ions and magnesium ions to obtain a first intensity, (b) contacting the mixture of step (a) with the sample; whereby the first intensity changes, (c) measuring the intensity of at least one fluorescence emission to obtain a second intensity and (d) deriving the concentration of magnesium ion in the sample based, in part, on the difference between the first and second intensities.

In some embodiments, the method determining magnesium ion in a sample comprising calcium ions and magnesium ions comprises contacting a device embodied herein with an aqueous solution that comprises magnesium and calcium ions, such as for example, a buffered solution and/or a biological fluid such as whole blood, plasma, serum, and/or urine. In another embodiment, the invention provides a method of determining magnesium ion in a sample comprising magnesium ions, calcium ions and a device embodied herein comprising a luminoionophore according to Formula (I).

In another embodiment, the invention provides a method of determining magnesium ion in a sample comprising magnesium ions, calcium ions and a device embodied herein comprising a luminoionophore according to Formula (II).

In another embodiment, the invention provides a method of determining magnesium ion in a sample comprising magnesium ions, calcium ions and a device embodied herein comprising a luminoionophore according to Formula (III).

In yet another embodiment, the invention provides a method of determining magnesium ion in a sample comprising magnesium ions, calcium ions and a device embodied herein comprising a known luminoionophore such as for example Magnesium Green.

Preparation of the Compounds of the Invention

Those skilled in the art will recognize that there are a variety of methods available to synthesize molecules represented in the claims. One general strategy is outlined herein, but is in no way meant to limit the scope of the claims.

EXAMPLE 1

Synthesis of Mg2

A mixture of Mg1 (100 g, 0.72 mol) and Pd(OH)$_2$/C (10 g, 10%) in THF (1 L) was hydrogenated at 50° C. at normal pressure for 16 h, and then Pd(OH)$_2$/C was filtered and washed with hot THF (200 mL), the filtrate was evaporated to dryness to give 79 g of Mg2 as a white solid (100% yield).

EXAMPLE 2

Synthesis of Mg3

Mg2 (79 g, 0.72 mol), NaOH (50 g, 1.25 mol) and sodium chloroacetate (313 g, 2.69 mol) were dissolved in water (290 mL), the mixture was heated to 90° C. A solution of NaOH (100 g, 2.5 mol) in water (100 mL) was added dropwise over 30 min. After addition, the mixture was heated at reflux for 2 h, and then cooled to 15° C. by an ice bath. The mixture was acidified to pH=2 by 4 N HCl (about 1.1 L). The mixture was extracted with EA(4*200 mL), the EA layer was combined and dried over Na$_2$SO$_4$ then evaporated to dryness. The residual was crystallized with MTBE (250 mL) to give 158 g of Mg3 as a white solid (77% yield).

EXAMPLE 3

Synthesis of Mg4

To a mixture of Mg3 (130 g, 0.46 mol) in EtOH (2600 mL) was added SOCl$_2$ (273 g, 2.29 mol) slowly. After addition, the mixture was heated at reflux overnight. The mixture was evaporated to dryness, and then the residual was dissolved in EA (2 L). The EA layer was washed with sat. Na$_2$CO$_3$ (aq.) (200 mL) and then brine (200 mL), dried over Na$_2$SO$_4$, evaporated to dryness to give 160 g of Mg4 as an oil (95% yield) (TLC: Petrol ether:EA=2:1, R$_f$=0.3).

EXAMPLE 4

Synthesis of Mg5

To a mixture of Mg4 (50 g) and urotropine (21 g) in AcOH (250 mL) was added TFA (50 mL), and then the mixture was stirred at 90° C. for 6 h under an atmosphere of N$_2$ gas. The solvent was evaporated and the residual was dissolved in EA (600 mL). The EA layer was washed with sat. Na$_2$CO$_3$ (aq.) (100 mL) and then brine (50 mL), dried over Na$_2$SO$_4$, evaporated to dryness. The residual was separated by column chromatography to give 17 g of Mg5 as an off-white solid (32% yield) (TLC: Petrol ether:EA=2:1, R$_f$=0.6, clean spot on TLC without Mg4).

EXAMPLE 5

Synthesis of Mg6

-continued

A mixture of Mg5 (5 g, 12.64 mmol) in MeNO₂ (30 mL) was added DBU (0.2 g, 1.3 mmol) at 25° C. After addition, the mixture was stirred for 30 min. The excessive MeNO₂ was evaporated under reduced pressure. The residual was added 100 mL of toluene and evaporated to dryness again. The residual was separated by column chromatography to give 3.2 g of Mg6 as a yellow solid (55% yield) (TLC: Petrol ether: EA=2:1, R$_f$=0.3, clean spot on TLC without Mg5).

EXAMPLE 6

Synthesis of Mg7

A mixture Mg6 (1.5 g, 3.3 mmol), Boc₂O (3.96 mmol), Raney Ni (0.5 g) in EtOH (20 mL) was hydrogenated at <15° C. overnight. The catalyst was filtered off and the residual was evaporated to dryness, the residual was purified over column chromatography to give 1.5 g of Mg7 as a clear oil (86% yield) (TLC: Petrol ether:EA=1:1, R$_f$=0.4, clean spot on TLC without Mg6).

EXAMPLE 7

Synthesis of Mg8

To a solution of Mg7 (18 g, 34.2 mmol), triethyl amine (5.2 g, 51.3 mmol) and DMAP (0.9 g) in 180 mL of dichloromethane was added acetic anhydride (102 g, 34.2 mmol) at 0° C. The reaction mixture was stirred overnight. It was quenched with 50 mL of water and extracted with dichloromethane (3*200 mL). It was dried over Na₂SO₄, evaporated to dryness. The residual was purified over column chromatography to give 7.6 g of Mg8 as a clear oil (39.2% yield) (TLC: Petrol ether:EA=2:1, R$_f$=0.4, clean spot on TLC without Mg7).

EXAMPLE 8

Synthesis of Mg9

17

Mg9

A solution Mg8 (7.5 g, 13.2 mmol) in EtOH (75 mL) was hydrogenated with Pd/C (1.5 g) overnight. The catalyst was filtered off and the residual was evaporated to dryness to give 6.7 g of Mg9 as a clear oil (100% yield) (TLC: Petrol ether: EA=2:1, $R_1$=0.3, clean spot on TLC without Mg8).

EXAMPLE 9

Synthesis of Mg10

18

A solution of Mg9 (6.6 g, 12.9 mmol) and trifluoroacetic acid (40 mL) in 40 mL of dichloromethane was stirred overnight and evaporated to give 5.5 g of Mg10 (clean spot on TLC without Mg9).

EXAMPLE 10

Synthesis of Opti-Target-5

Opti-Target-5

A mixture of Mg10 (4.4 g, 8.4 mmol), compound 10A (3.6 g, 8.4 mmol) and DIPEA (13.3 mL) in NMP (33 mL) was stirred at 100° C. for 3 days under $N_2$. The mixture was poured into water (10 mL), extracted with EA (3*50 mL). The combined EA layer was washed with sat. $Na_2CO_3$ (aq.) (3*10 mL), and then it was washed with brine (10 mL), dried over $Na_2SO_4$, evaporated to dryness. The residual was purified over column chromatography to give 1.1 g of Opti-Target-5 as a yellow solid (17% yield) (TLC: Petrol ether: EA=1:1, $R_f$=0.3).

Determination of Luminescence Properties

In the context of the present invention the expression "measuring the luminescence" refers to the measurement of any luminescence property, including the measurement of luminescence intensity, time-resolved measurements of decaying luminescence intensity and phase modulation measurements.

The determination of the ion in the sample utilizing the measured luminescence can be based on luminescence intensity or on luminescence decay time.

Methods of determining ions by measuring luminescence of various luminoionophores are described, for example, in U.S. Pat. Nos. 6,211,359; 5,959,491; 6,171,866, each of which is hereby incorporated by reference.

Production of the Sensor

Luminionophore (Magnesium dye) was covalently linked to 3-amino-2-hydroxypropyl cellulose (AHPC) fiber by DCC coupling. The fiber is then washed to remove the free dye, and then dried and sieved @ 25 μm. The magnesium fiber was then mixed with D4 hydrogel, and kept stirring for at least 20 hours at room temperature (RT) to get a uniform dispersion. The topcoating suspension was prepared by mixing 1, 2-bis (o-aminophenoxy) ethane-N,N,N',N' tetrasodium salt (BAPTA) and carbon black into D6 hydrogel, which was stirred for at least 20 hours at RT to achieve a uniform dispersion.

The coating suspension was coated on polyester based Melinex® 505 sheet which has a dry thickness of 125 μm. The indicator suspension was applied on the Melinex®, and evenly spread at a wet thickness of 100 μm. The layer was dried for at least 30 minutes to evaporate the water and ethanol in the hydrogel resulting in a dry thickness of indicator layer of about 7 μm to 8 μm. The topcoating suspension was then applied with the same equipment, dried for at least 30 minutes, resulting in a topcoating with a dry thickness at about 7 to 4 μm.

A sheet of PSA (pressure sensitive adhesive) was attached to the back of the Melinex® 505 sheet. Sensors were then punched from the Melinex and set directly into the channel 5 well of OPTi LION cassettes and fixed by the adhesive on the back of the sensor. Covers were then welded onto the cassettes. The cassettes were then pouched with 0.5 g molecular sieve and baked in 41° C. for 1 week. After baking, the iMg cassettes were stored in refrigerator (about 4° C.) until testing.

Sample Preparation
H-buffer Preparation:

4-(2-hydroxyethyl)-1-piperazineethanesulfonic acid (HEPES), a zwitterionic organic chemical buffering agent and one of the twelve Good's buffers is widely used in cell culture, largely because it is better at maintaining physiological pH. In this study, HEPES buffer was prepared as a stock solution with a pH of 7.4, and the following ion concentrations: [$Na^+$] 146 mM, [$K^+$] 5 mM, and [$Cl^-$] 104 mM. Sodium, potassium and chloride are the major ion analyte in human blood, and the above concentrations are the normal levels in a healthy human being. The buffer was then spiked with $MgCl_2$ to obtain a serial concentration of $Mg^{2+}$ of 0.1 mM, 0.25 mM, 0.5 mM, 1 mM and 2 mM. Each of the five buffers was separated into two parts, one part was spiked with $CaCl_2$ to reach a concentration of $Ca^{2+}$ of 1.2 mM, and the other part was kept unchanged with a concentration of $Ca^{2+}$ of 0 mM. The normal concentration of $Ca^{2+}$ in human blood is 1.2 mM. The response of the Mg sensor at various [$Mg^{2+}$] was measured to determine each sensor's sensitivity and linearity. By comparing the responses of Mg sensor at various a concentrations of $Ca^{2+}$ the blocking effect of BAPTA was studied.

Whole Blood Sample:

Fresh whole blood sample was obtained from healthy human subjects. Whole blood sample was either diluted with H-buffers which contains no $Mg^{2+}$ to lower the concentration of $Mg^{2+}$ in the samples, or spiked with $MgCl_2$ to raise the concentration of $Mg^{2+}$ in the samples. Four levels of [$Mg^{2+}$] samples were prepared to observe demonstrate response of the Mg sensor to concentrations of $Mg^{2+}$ in the blood samples. Each of the above four samples was divided into two parts, one part was then spiked with $CaCl_2$ to reach 2.4 mM of [$Ca^{2+}$], the other part is remain unchanged. Thus two levels of [$Ca^{2+}$] samples were prepared.

Sample Preparation iMg cassettes were tested with an OPTi LION™ Stat Electrolyte Analyzer. First, the cassettes were removed from the refrigerator, and warmed to RT for at least one hour. Next, the cassettes were placed into the instrument, and a sipper was attached onto the cassette for sample aspiration. The testing program was begun, wherein the instrument illuminates a blue light-emitting diodes (LED) and measures the dry intensity of the luminionophore for 60 seconds. Next, the sample was attached to the sipper and the peri-pump installed in the instrument aspirates the sample into the cassettes. The sample contacts the topcoating first, and diffuses through the topcoating and reaches the indicator. $Mg^{2+}$ binds the luminionophore and "switches off" the quenching of the fluorescence. The fluorescence intensities are dependant on the amount of $Mg^{2+}$ bound to the luminionophore. A higher $Mg^{2+}$ concentration can result into higher fluorescence intensity. The instrument will measure and record the wet intensity for 120 seconds. Every 2 seconds the instrument will output 1 intensity reading. So totally there are 30 dry intensity readings and 60 wet intensity readings will be recorded.

Data Analysis

The results of the measurement were exported into a spreadsheet, with 30 dry intensity readings followed by 60 wet intensity readings. The averages were calculated of the last 10 dry intensity readings and use this value as the "dry intensity" for later calculation. The 60 wet intensities were then divided by the "dry intensity" to calculate the normalized intensity. The average normalized intensity from second 56 to 64 was then calculated to determine the wet/dry ratios used for sensor performance evaluation. Higher ratios indicate higher concentration of sample $Mg^{2+}$.

Sensor Sensitivity and Precision Test

Figure 1:
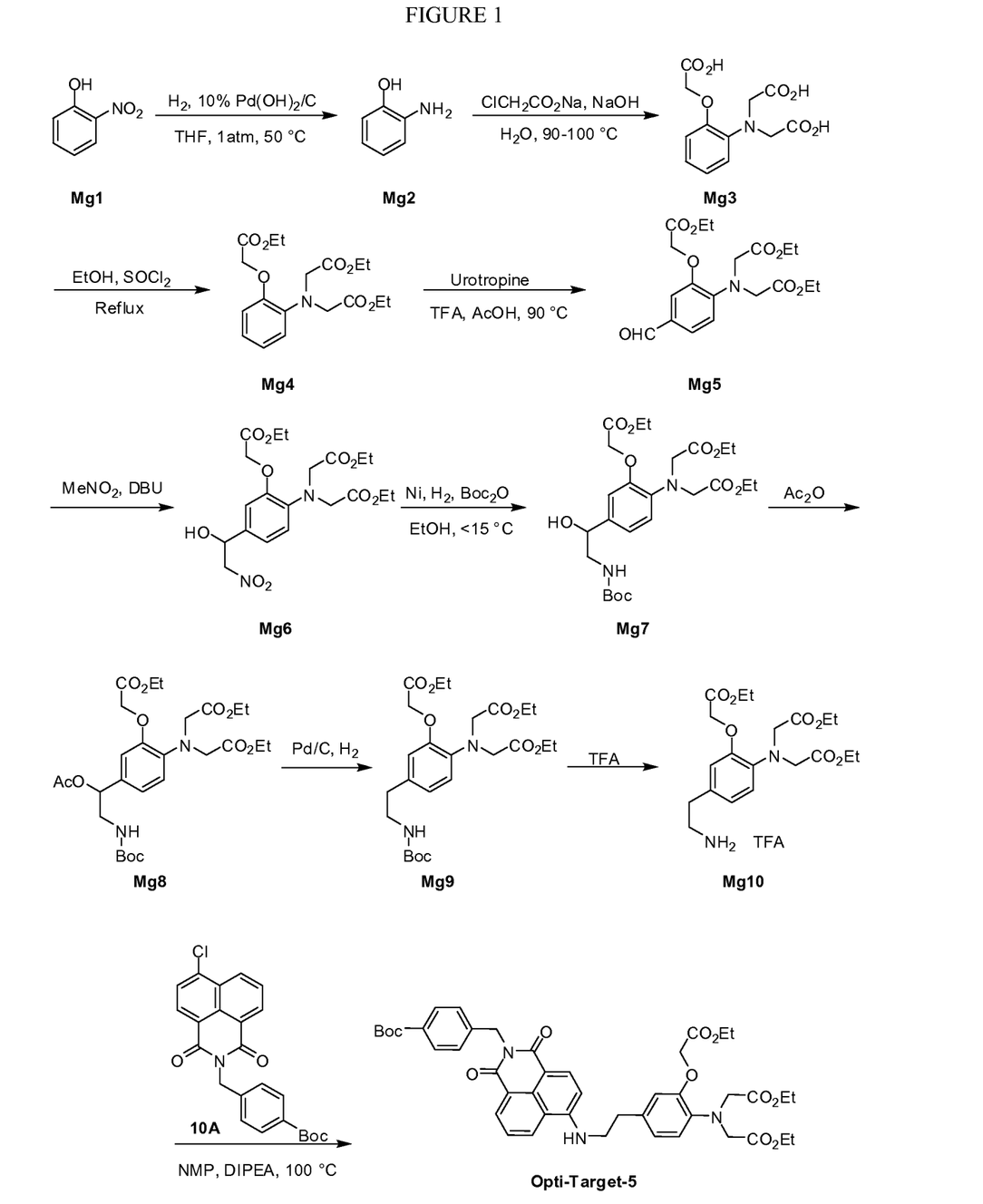
FIG. 1 is an illustration of the synthetic pathway for a novel magnesium luminoionophore.
Figure 2:
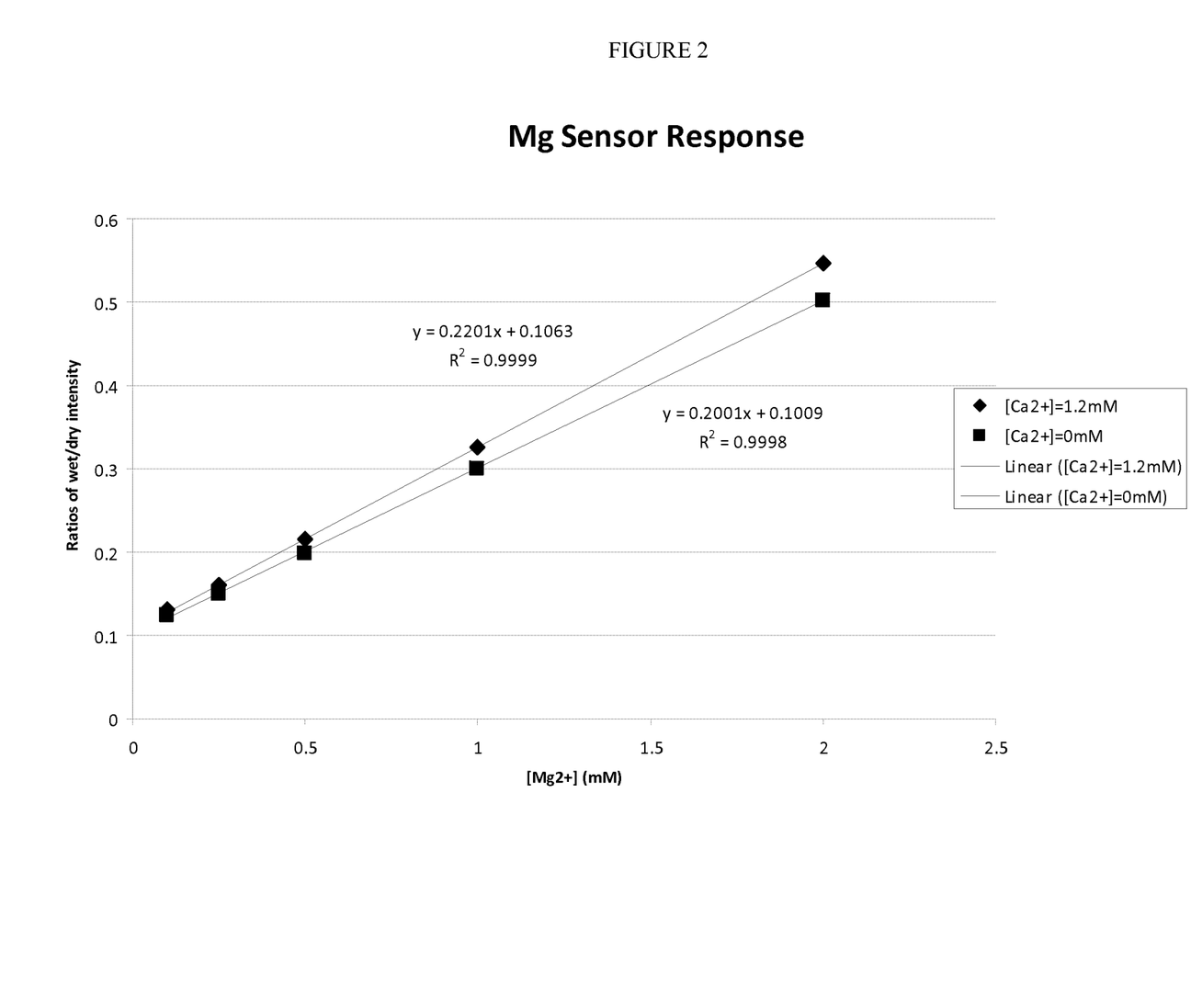
FIG. 2 is a graph illustrating the Mg sensor response with H-buffers at 5 concentrations of $Mg^{2+}$ and 2 concentrations of $Ca^{2+}$.

Mg sensors were made according to the procedure described before, and tested with H-buffers of 10 repetitions at each level. FIG. 1 showed the ratios calculated based on the above-mentioned data analysis method vs. the [$Mg^{2+}$]. Ratios at different concentrations of $Mg^{2+}$, from 0.1 mM to 2 mM, are very well separated. Meanwhile, the good linearity is achieved with the R2 to be 0.999. At two levels of [$Ca^{2+}$], the Mg sensors' responses are very similar, which suggests that the $Ca^{2+}$ diffusion is efficiently blocked by BAPTA. See FIG. 2 which demonstrates Mg sensors' response with H-buffers at five levels of [$Mg^{2+}$] and two levels of [$Ca^{2+}$].

Coefficient of Variation (CV) was calculated by dividing the average of the ratios by standard deviation. A smaller CV means more uniform coating and greater precision. Table 1 shows the CV of the ratios of the iMg sensors measured with H-buffers at five levels of [$Mg^{2+}$] and two levels of [$Ca^{2+}$]. All ten CVs in the study were less than 4% indicating a good precision of the Mg sensors. The ratio of wet/dry intensity for different $Mg^+$ and $Ca^{2+}$ concentrations is plotted in FIG. 2.

TABLE 1

CV (%) of the ratios measured with H-buffers

| [Mg2+] (mM) | 0 mM Ca2+ | 1.2 mM Ca2+ |
|---|---|---|
| 0.1 | 1.36 | 1.87 |
| 0.25 | 1.65 | 1.44 |
| 0.5 | 1.32 | 2.57 |
| 1 | 3.00 | 2.28 |
| 2 | 3.25 | 3.39 |

Sensor Accelerated Storage Stability Test

The iMg cassettes were stored at 41° C. for two weeks, and tested at T=0, T=1 week and T=2 week to measure the stability. H-buffers with five levels of [$Mg^{2+}$] and two levels of [$Ca^{2+}$] were used in this experiment. At least five repetitions were done with each buffer. Table 2 and Table 3 show the ratios measured with H-buffers at 1.2 mM $Ca^{2+}$ and 0 mM $Ca^{2+}$, respectively. No significant difference of the ratios was observed from T=0, T=1 week and T=2 week. Both the Mg dye and BAPTA proved to be stable during the storage period.

TABLE 2

Ratios of Mg sensors tested with H-buffer contains 1.2 mM Ca²⁺

| $[Mg^{2+}]$ (mM) | T = 0 | T = 1 week | T = 2 weeks |
|---|---|---|---|
| 0.1 | 0.13 | — | — |
| 0.25 | 0.16 | 0.16 | 0.16 |
| 0.5 | 0.22 | 0.21 | 0.22 |
| 1 | 0.33 | 0.32 | 0.33 |
| 2 | 0.55 | | |

TABLE 3

Ratios of Mg sensors tested with H-buffer contains 0 mM Ca²⁺

| $[Mg^{2+}]$ (mM) | T = 0 | T = 1 week | T = 2 weeks |
|---|---|---|---|
| 0.1 | 0.12 | — | — |
| 0.25 | 0.15 | 0.15 | 0.15 |
| 0.5 | 0.20 | 0.20 | 0.20 |
| 1 | 0.30 | 0.30 | 0.29 |
| 2 | 0.50 | | |

* iMg sensor tested with whole blood sample

Blood sample contains dissipated proteins, glucose, mineral ions, hormones, platelets and blood cells, etc., thereby resulting in a much more complicated fluid compared to a buffer. Fresh whole blood samples were prepared according to the procedure described above. Concentrations of $Ca^{2+}$ and $Mg^{2+}$ in the blood samples were measured by NOVA® Critical Care Xpress Analyzer. Table 4 shows the $[Mg^{2+}]$ and $[Ca^{2+}]$ measured by NOVA®. Sample 1 and 2, 3 and 4, 5 and 6, 7 and 8 should have the same $[Mg^{2+}]$ and different $[Ca^{2+}]$ because $CaCl_2$ was spiked into samples 1, 3, 5 and 7 to get samples 2, 4, 6 and 8.

TABLE 4

NOVA readings of [Ca²⁺] and [Mg²⁺] of whole blood samples

| Sample # | $[Mg^{2+}]$ (mM) | $[Ca^{2+}]$ (mM) |
|---|---|---|
| 1 | 0.28 | 1.1 |
| 2 | 0.38 | 2.02 |
| 3 | 0.63 | 1.24 |
| 4 | 0.75 | 2.12 |
| 5 | 0.94 | 1.26 |
| 6 | 1.1 | 2.07 |
| 7 | 1.59 | 1.22 |
| 8 | 1.73 | 2.11 |

Figure 3:
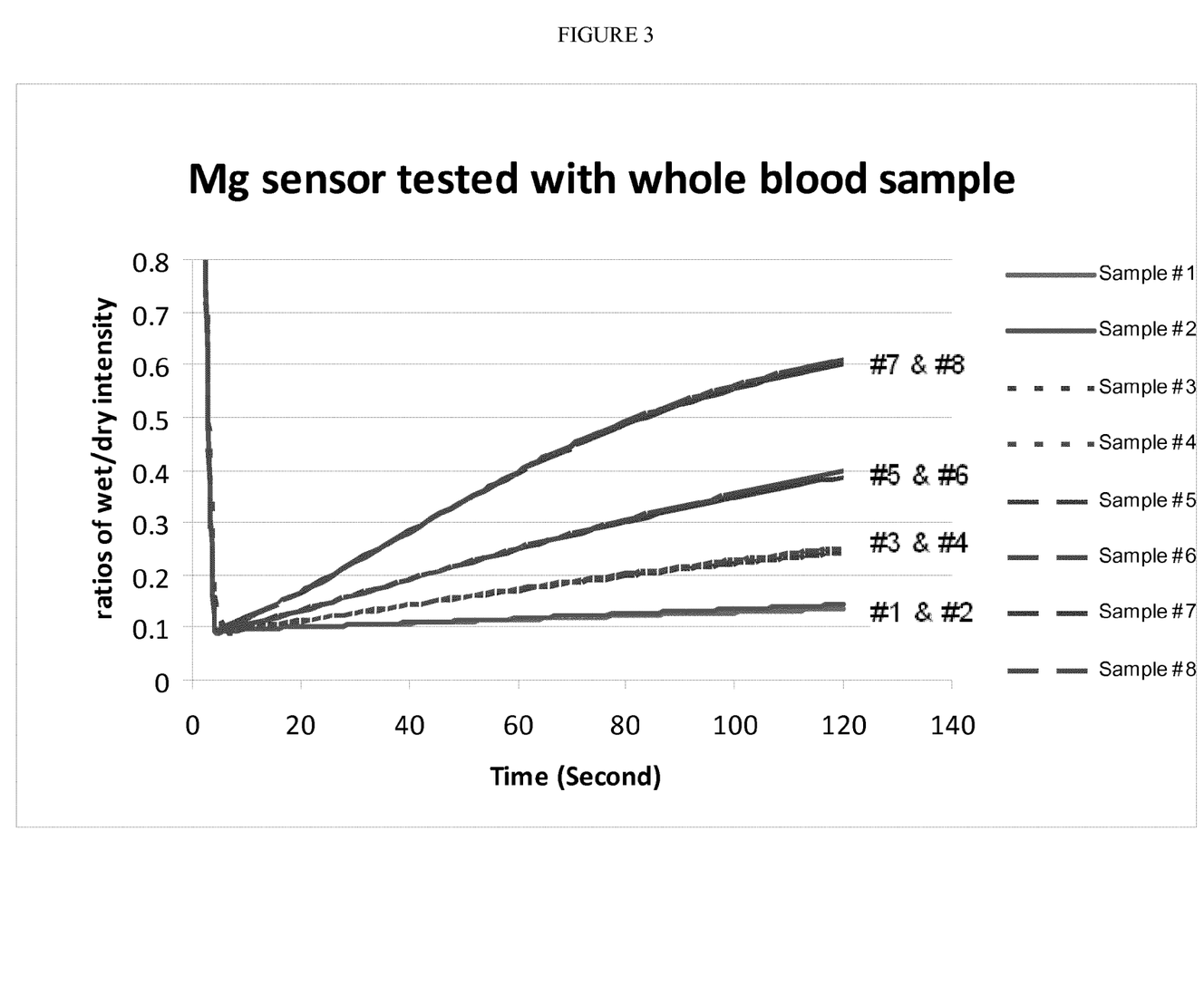
FIG. 3 is an illustration of the ratios of blood sample measured with a Mg sensor.
Figure 4:
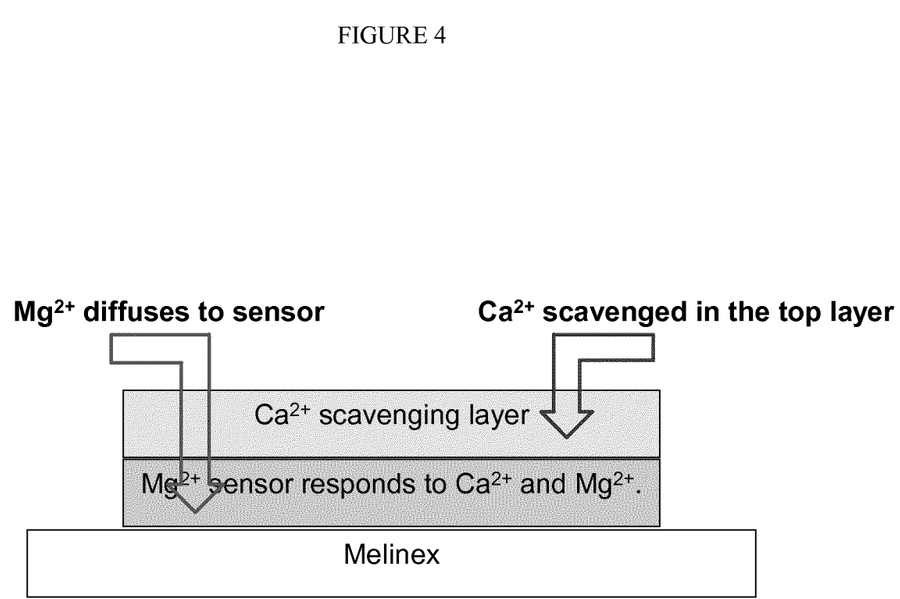
FIG. 4 is a schematic of the layers of a device embodied herein.

FIG. 3 shows that at different $[Mg^{2+}]$, the response curves are very well separated, which indicates a good sensitivity of iMg sensor when measured with whole blood sample. Meanwhile, the results showed that the measured ratios of the samples with same $[Mg^{2+}]$ but different $[Ca^{2+}]$ are very close in value, indicating that the BAPTA efficiently blocked the $Ca^{2+}$ in the blood sample. This is further illustrated in FIG. 3, which shows the ratios of blood sample measured with Mg sensor.

We claim:

1. A device for selectively measuring the presence of magnesium ions comprising:
a substrate;
a sensor layer comprising a luminoionophore that is capable of binding magnesium ions and that is optionally immobilized on a solid support; and
a scavenging layer that preferentially binds to calcium ions in the presence of both magnesium ions and calcium ions;
wherein the luminoionophore exhibits luminescence at a first intensity and wherein upon contacting said device with a solution containing magnesium ions the luminoionophore exhibits luminescence at a second intensity that is different from the first intensity in an amount that is in proportion to the concentration of magnesium ion present in the solution; and
wherein the luminoionophore conforms to the following formula I:

(I)

wherein,
A, B, and C are independently selected from the group consisting of hydrogen, —OCH₂COOR', and —N(CH₂COOR')₂,
wherein one or more of A, B and C is independently selected from the group consisting of —OCH₂COOR' and —N(CH₂COOR')2,
wherein R' is selected from the group consisting of hydrogen, $C_1$-$C_{12}$-alkyl, and a cation;
X and Y, in each instance where they appear, are independently selected from the group consisting of hydrogen, hydroxyl, halogen, ethoxy, methoxy, amine and —COOR';
v is an integer selected from 0, 1, 2, 3 and 4; and
Z is a luminophoric moiety of Formula (a):

(a)

wherein,
$R^3$, $R^4$, $R^5$, $R^6$, $R^7$ $R^8$, and $R^9$ are independently selected from the group consisting of hydrogen, a lipophilic group, a hydrophilic group and a reactive group for coupling to a polymer; wherein at least one of $R^3$, $R^4$, $R^5$, $R^6$, $R^7$, and $R^8$ is a —NH— group through which Z is bound to the group —(CXY)ᵥ—.

2. The device according to claim 1 wherein the luminoionophore comprises an ionophore having one or more chelating moieties capable of binding to magnesium, and a luminophoric moiety.

3. The device according to claim 1, wherein Z has the general formula (a) and one of $R^5$ and $R^6$ is —NH and the other is selected from the group consisting of hydrogen, a lipophilic group, a hydrophilic group and a reactive group for coupling to a polymer.

4. The device according to claim 1 wherein the sensor layer comprises a luminoionophore of the formula (II):

(II)

wherein,
each instance of R is independently selected from the group consisting of hydrogen, $C_1$-$C_{12}$-alkyl, and a cation;
A is $(CXY)_n$ wherein n is an integer selected from 0, 1, 2, 3, and 4 and
wherein X and Y, in each instance where they appear, are independently selected from the group consisting of hydrogen, hydroxyl, halogen, ethoxy, methoxy, amine and —COOR';
Z is NH or O; and
Q is a hydrogen, $C_1$-$C_{12}$-alkyl, cation or solid support.

5. The device according to claim 4 wherein the sensor layer comprises a luminoionophore of the formula (III)

(III)

wherein,
each instance of R is independently hydrogen, $C_1$-$C_{12}$-alkyl, and cation
A is —(CHOH)— or a bond and
Q is a hydrogen, $C_1$-$C_{12}$-alkyl, cation or solid support.

6. The device according to claim 1 wherein the substrate comprises a high-clarity polymer.

7. The device according to claim 1 wherein the substrate comprises high-clarity polyester film which is pretreated to promote adhesion.

8. The device according to claim 1 wherein the scavenging layer comprises a compound having one or more chelating moieties capable of selectively binding calcium ions in the presence of a mixture of calcium ions and magnesium ions.

9. The device according to claim 8 wherein the scavenging layer comprises a compound selected from the group of 1,2-bis(o-aminophenoxy)ethane-N,N,N',N'-tetraacetic acid, ethylene glycol tetraacetic acid, sodium oxalate, a salt, and/or mixtures thereof.

10. The device according to claim 9 wherein the scavenging layer comprises a mixture of 1,2-bis(o-aminophenoxy)ethane-N,N,N',N'-tetraacetic acid represented by the general Formula (IV)

(IV)

wherein R is selected from H or a cation.

11. A device for selectively measuring the presence of magnesium ions comprising:
a substrate;
a sensor layer comprising a luminoionophore that is capable of binding magnesium ions and that is optionally immobilized on a solid support; and
a scavenging layer that preferentially binds to calcium ions in the presence of both magnesium ions and calcium ions;
wherein the luminoionophore exhibits luminescence at a first intensity and wherein upon contacting said device with a solution containing magnesium ions the luminoionophore exhibits luminescence at a second intensity that is different from the first intensity in an amount that is in proportion to the concentration of magnesium ion present in the solution; and
wherein the luminoionophore is potassium 2,2'-(4-(3-carboxylato-4-(2,7-dichloro-6-oxido-3-oxo-3H-xanthen-9-yl)benzamido)-2-(carboxylatomethoxy)phenylazanediyl)diacetate, and mixtures thereof.

12. The device according to claim 11 wherein the luminoionophore is potassium 2,2'-(4-(3-carboxylato-4-(2,7-dichloro-6-oxido-3-oxo-3H-xanthen-9-yl)benzamido)-2-(carboxylatomethoxy)phenylazanediyl)diacetate.

13. A luminoionophore of the general Formula (I)

wherein,

A, B, and C are independently selected from the group consisting of hydrogen, —OCH$_2$COOR', and —N(CH$_2$COOR')$_2$,
  wherein one or more of A, B and C is independently selected from the group consisting of —OCH$_2$COOR' and —N(CH$_2$COOR')2,
  wherein R' is selected from the group consisting of hydrogen, C$_1$-C$_{12}$-alkyl, and a cation;

X and Y, in each instance where they appear, are independently selected from the group consisting of hydrogen, hydroxyl, halogen, ethoxy, methoxy, amine and —COOR';

v is an integer selected from 0, 1, 2, 3 and 4; and

Z is a luminophoric moiety of Formula (a)

wherein,

R$^3$, R$^4$, R$^5$, R$^6$, R$^7$ R$^8$, and R$^9$ are independently selected from the group consisting of hydrogen, a lipophilic group, a hydrophilic group and a reactive group for coupling to a polymer; wherein at least one of R$^3$, R$^4$, R$^5$, R$^6$, R$^7$, and R$^8$ is a —NH-group through which Z is bound to the group —(CXY)$_v$—.

14. The luminoionophore according to claim 13, wherein Z has the general formula (a) and one of R$^5$ and R$^6$ is —NH and the other is selected from the group consisting of hydrogen, a lipophilic group, a hydrophilic group and a reactive group for coupling to a polymer.

15. The luminoionophore according to claim 13, wherein the luminoionophore has a structure of the formula (II):

wherein,
  each instance of R is independently hydrogen, C$_1$-C$_{12}$-alkyl, and cation;
  A is (CXY)$_n$ wherein n is an integer selected from 0, 1, 2, 3, and 4 and
  X and Y, in each instance where they appear, are independently selected from the group consisting of hydrogen, hydroxyl, halogen, ethoxy, methoxy, amine and —COOR';
  Z is NH or O; and
  Q is a hydrogen, C$_1$-C$_{12}$-alkyl, cation or solid support.

16. A method of determining the concentration of magnesium ions in a sample comprising:
  (a) measuring a fluorescence emission of a mixture comprising a luminoionophore that is capable of binding magnesium ions and a compound that displays a preferential binding affinity for calcium ions when in the presence of both calcium ions and magnesium ions to obtain a first intensity;
  (b) contacting the mixture of step (a) with the sample; whereby the first intensity changes;
  (c) measuring the intensity of at least one fluorescence emission to obtain a second intensity;
  (d) deriving the concentration of magnesium ion in the sample based, in part, on the difference between the first and second intensities;
  wherein the luminoionophore conforms to the following formula I:

wherein,

A, B, and C are independently selected from the group consisting of hydrogen, —OCH$_2$COOR', and —N(CH$_2$COOR')$_2$,
  wherein one or more of A, B and C is independently selected from the group consisting of —OCH$_2$COOR' and —N(CH$_2$COOR')2, wherein R' is selected from the group consisting of hydrogen, $C_1$-$C_{12}$-alkyl, and a cation;

X and Y, in each instance where they appear, are independently selected from the group consisting of hydrogen, hydroxyl, halogen, ethoxy, methoxy, amine and —COOR';

v is an integer selected from 0, 1, 2, 3 and 4; and

Z is a luminophoric moiety of Formula (a)

(a)

wherein, $R^3$, $R^4$, $R^5$, $R^6$, $R^7$ $R^8$, and $R^9$ are independently selected from the group consisting of hydrogen, a lipophilic group, a hydrophilic group and a reactive group for coupling to a polymer; wherein at least one of $R^3$, $R^4$, $R^5$, $R^6$, $R^7$, and $R^8$ is a —NH-group through which Z is bound to the group —(CXY)$_v$—.

17. The method according to claim 16, wherein Z has the general formula (a) and one of $R^{12}$ and $R^{13}$ is —NH and the other is selected from the group consisting of hydrogen, a lipophilic group, a hydrophilic group and a reactive group for coupling to a polymer.

18. The method according to claim 16, wherein the luminoionophore is a compound of Formula (II)

(II)

wherein, each instance of R is independently hydrogen, $C_1$-$C_{12}$-alkyl, and cation;

A is (CXY)$_n$ wherein n is an integer selected from 0, 1, 2, 3, and 4 and wherein each instance of X and Y is independently selected from the group consisting of hydrogen, hydroxyl, halogen, ethoxy, methoxy, amine and —COOR;

Z is NH or O; and

Q is a hydrogen, $C_1$-$C_{12}$-alkyl, cation or solid support.

19. The method according to claim 16, wherein the luminoionophore is a compound of Formula (III)

(III)

wherein, each instance of R is independently hydrogen, $C_1$-$C_{12}$-alkyl, and cation;

A is —(CHOH)— or a bond; and

Q is a hydrogen, $C_1$-$C_{12}$-alkyl, cation or solid support.

20. The method according to claim 16, wherein the sample is a biological fluid.

21. The method according to claim 20, wherein the biological fluid is selected from the group consisting of whole blood, plasma, serum, and urine.

* * * * *